Figure 1:
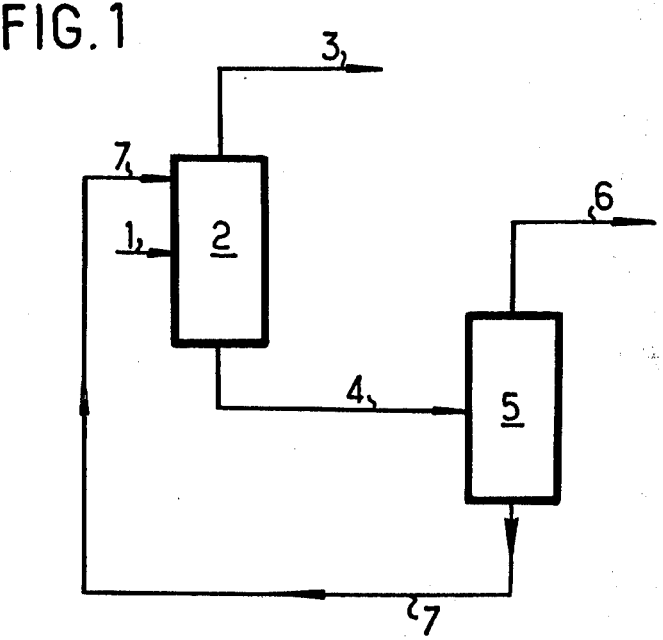

United States Patent [19]

Becuwe

[11] 4,121,978

[45] Oct. 24, 1978

[54] METHOD OF SEPARATING CHLORINATED ALIPHATIC HYDROCARBONS FROM MIXTURES THEREOF, BY EXTRACTIVE DISTILLATION

[75] Inventor: Jacques Becuwe, Fontenay-sous-Bois, France

[73] Assignee: Rhone-Progil, Courbevoie, France

[21] Appl. No.: 734,083

[22] Filed: Oct. 20, 1976

Related U.S. Application Data

[63] Continuation of Ser. No. 564,328, Apr. 2, 1975, abandoned, which is a continuation of Ser. No. 437,370, Jan. 28, 1974, abandoned.

[30] Foreign Application Priority Data

Jan. 30, 1973 [FR] France ............................ 73.03178

[51] Int. Cl.$^2$ ............................................. B01D 3/34
[52] U.S. Cl. .............................. 203/58; 203/60; 203/62; 203/64; 203/57; 260/654 S; 260/652 P
[58] Field of Search ................ 260/652 P, 654 S; 203/57–64

[56] References Cited

U.S. PATENT DOCUMENTS

| | | | |
|---|---|---|---|
| 2,212,107 | 8/1940 | Yabroff | 260/654 S |
| 2,357,028 | 8/1944 | Shiras et al. | 203/56 |
| 2,858,347 | 10/1958 | Hutchings | 260/654 S |
| 3,113,079 | 12/1963 | Bergeron et al. | 203/64 |
| 3,427,357 | 2/1969 | Gramont et al. | 260/652 P |
| 3,689,373 | 9/1972 | Hutchinson | 203/58 |
| 3,809,724 | 5/1974 | Golden | 203/67 |

Primary Examiner—Norman Yudkoff
Attorney, Agent, or Firm—McDougall, Hersh & Scott

[57] ABSTRACT

A method for the partial or total separation by extractive distillation of $C_1$ to $C_3$ clorinated aliphatic hydrocarbons from mixtures of at least two such chlorinated hydrocarbons. The mixture of the chlorinated hydrocarbons is distilled in the presence of one or more other organic compounds having a boiling temperature higher than the substances to be separated, and selected from the group comprising saturated polyols, ethylene carbonate, propylene carbonate, dimethyl formamide, furfural, N-methylpyrrolidone, cyclohexanone, dimethylsulfoxide and, preferably, sulfolane and alkylsulfolanes in which the alkyl group is $C_1$ or $C_2$; use of this method for the separation of mixtures containing or essentially consisting of trichlorethylene and 1,2-dichloroethane.

4 Claims, 2 Drawing Figures

METHOD OF SEPARATING CHLORINATED ALIPHATIC HYDROCARBONS FROM MIXTURES THEREOF, BY EXTRACTIVE DISTILLATION

This is a continuation of application Ser. No. 564,328 filed Apr. 2, 1975, now abandoned, which is a continuation of Ser. No. 437,370 filed Jan. 28, 1974, now abandoned.

The present invention relates to a method for the partial or total separation by extractive distillation of $C_1$ to $C_3$ chlorinated aliphatic hydrocarbons from mixtures of at least two of such compounds.

The operation of separating mixtures of certain chlorinated aliphatic hydrocarbons having up to 3 carbon atoms and more particularly, mixtures of trichloroethylene and 1,2-dichloroethane, perchloroethylene and 1,1,2-trichloroethane, carbon tetrachloride and 1,2-dichloroethane and 1,1,1-trichloroethane, and 1,2-dichloroethane is very difficult to carry out by conventional fractionated distillation, either because of the formation of an azeotrope, or because of the low relative volatility of the constituents of such mixtures.

For example, the separation of trichloroethylene from 1,2-dichloroethane is very important for producing vinyl chloride and $C_2$ and/or $C_1$ chlorinated aliphatic hydrocarbons as solvents.

It is known that 1,2-dichloroethane and trichloroethylene have boiling points which are very close (83.65° and 86.2° C. respectively), and that they form an azeotrope with 62 molar percent of 1,2-dichloroethane, distilling at 82.2° C. at atmospheric pressure. Because of this, it is impossible, by conventional distillation, to separate any mixtures of these two compounds into pure substances. It is also but possible to envisage a process of distillation in two columns operating at different pressures, since the azeotrope is of a virtually constant composition, dependent on pressure.

It is also known, that in some operations of separation which are difficult to carry out by simple distillation, for example in separating butenes and butane, butene and butadiene, and benzene and cyclohexane, separation can be effected by extractive distillation in the presence of a suitably selected other substance. In fact, some specific substances modify the possibilities of distillation, and permit separation thereof.

These other substances obviously vary according to the nature of the mixtures to be separated, and it is virtually impossible, when a problem is encountered in separating given substances, to foresee which other substances would be suitable for the separation operation.

The applicants have found, and therefore it is an object of this invention to provide, a group of substances which, when incorporated in mixtures of $C_1$ to $C_3$ chlorinated aliphatic hydrocarbons, permit partial or total separation thereof, under easy and highly satisfying conditions.

In accordance with the method of this invention, distillation of the mixtures to be separated is effected in the presence of one or more organic compounds having a boiling point temperature which is higher than that of the substances to be separated, and selected from the group of saturated polyols, ethylene carbonate, propylene carbonate, dimethylformamide, furfural, N-methylpyrrolidone, cyclohexanone, dimethylsulfoxide and, preferably, sulfolane and alkylsulfolanes, in which the alkyl group is $C_1$ or $C_2$.

The polyols which can be used include more particularly, diethylene glycol, triethylene glycol, tetraethylene glycol, dipropylene glycol and propane diols.

In the particular case of extractive distillation of a binary mixture, the other organic compound passes completely to the bottom of the column with one of the substances, or a mixture which contains a high proportion of said substance. The other substance or a mixture which contains a high proportion of the second substance will be in the distillate.

The liquid from the bottom of the column is then readily treated in a second column in which the said other organic compound is regenerated by conventional fractionated distillation.

The proportion of the other organic compound to be injected into a column for the extractive distillation of a mixture of $C_1$ to $C_3$ chlorinated aliphatic hydrocarbons can be varied, depending on several factors such as: the efficiency of the organic compound selected, the size of the column (number of plates) and operating conditions which have been set (rate of reflux, and pressure). In general, the above-mentioned proportion is at least 10% by weight and preferably at least equal to the weight of the mixture of chlorinated hydrocarbons.

The method of the invention can be used in general for mixtures of any proportions of $C_1$ to $C_3$ chlorinated aliphatic hydrocarbons.

For simplicity, the substances which are easily separable from the mixtures encountered in industrial installations are generally first drawn off, leaving the pairs of substances which are difficult to separate, in proportions which are present largely in the majority in the mixtures to be treated by the method according to the present invention.

Particular examples of mixtures which are difficult to separate, besides the mixture which contains or essentially consists of 1,2-dichloroethane and trichloroethylene, include, inter alia, mixtures of perchloroethylene and 1,1,2-trichloroethane, carbon tetrachloride and 1,2-dichloroethane, and 1,1,1-trichloroethane and 1,2-dichloroethane.

According to the invention, the extractive distillation operation can be carried out either at a pressure which is below atmospheric pressure, more particularly in a partial or total vacuum, or preferably, at atmospheric pressure.

In an advantageous embodiment of the invention, the other organic compound is recovered at a pressure which is below that used for the extractive distillation operation proper.

Figure 2:
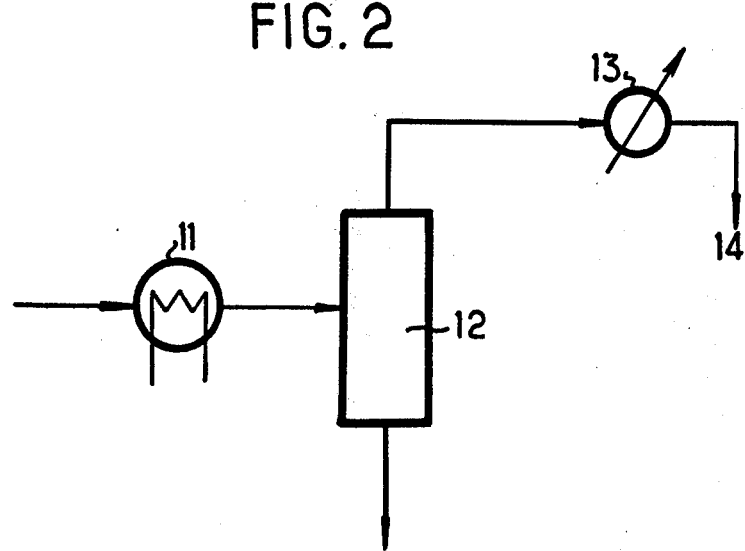

Accompanying FIG. 1 is a flow diagram of an installation for carrying out an embodiment of the separation method according to the invention; and FIG. 2 is a flow diagram for testing the efficiency of the other organic compound in separating the constituents of a mixture forming an azeotrope.

In FIG. 1, the mixture to be subjected to the extractive distillation operation is injected at 1 into a distillation column 2, at the top of which is injected the other organic compound 7. One of the two substances to be separated is collected at the head 3 of the column. The second substance passes from the bottom of the column to line 4, in mixture with the other organic compound, and thence is passed to a second column 5 wherein it is recovered, in pure form, at the head 6 of the column, while the other organic compound is discharged at the tail end of the column and is returned to the first column through 7.

The disappearance of the azeotrope in the presence of another organic compound can be noted, by introducing continuously into the boiler 11, in FIG. 2, a mixture comprising the substances to be separated, having the composition of the azeotrope thereof, and the other selected organic compound, then by continuously heating and partially vaporizing the mixture. The vapor-liquid mixture is then separated in the distillation column 12 and the vapor, condensed at 13, is collected at 14, while the liquid phase is recovered at the bottom of the column.

In the case where the organic compound selected does not have any effective action on separation, the two substances to be separated remain in the same relative proportion in the two effluents collected, which proportion is also the same as in the starting mixture.

On the other hand, when the organic compound selected breaks or strongly displaces the azeotrope, the above-mentioned relative proportion is different in the two effluent phases, and the relative "pseudo volatility" $\alpha$ of the substance A relative to the substance B can be defined by the relationship:

$$\alpha = \frac{\text{molar \% of } A/\text{molar \% of } B \text{ in the vapor phase}}{\text{molar \% of } A/\text{molar \% of } B \text{ in the liquid phase}}$$

the substance A being that in which the proportion has increased relative to the starting mixture, in the vapor phase collected.

The following examples illustrate the invention but do not limit it:

EXAMPLE 1

The apparatus illustrated in FIG. 1 comprises a first column 2 which is 70 mm in diameter and which comprises 70 plates, the column operating at atmospheric pressure. At a position towards the lower third of the column, 2kg/h of a liquid mixture comprising 55 parts by weight of 1,2-dichloroethane and 45 parts by weight of trichloroethylene is injected at 20° C. into the column. Towards the top of the column, 258 kg/h of sulfolane is injected at 85° C. The rate of reflux is 5. The head product from the column is composed of:

8.90 kg/h of trichloroethylene,
1.2 g/h of 1,2-dichloroethane,
0.052 g/h of sulfolane, and the effluent from the boiler comprises:

11 kg/h of 1,2-dichloroethane,
0.1 kg/h of trichloroethylene,
258 kg/h of sulfolane.

The latter effluent is used to feed the second column 5 which operates at a residual pressure of 50 mm and which comprises 10 plates; the rate of reflux is 2.

At the head end of this column, about 11 kg/h of a mixture is collected, as follows:

11 kg/h of 1,2-dichloroethane,
0.01 kg/h of trichloroethylene,
0.03 g/h of sulfolane.

The recycled sulfolane contains 2.5 ppm of 1,2-dichloroethane, and no trichloroethylene.

EXAMPLE 2

In the apparatus shown in FIG. 2, there is introduced into the boiler 11 a mixture of dimethyl sulfoxide, trichloroethylene and 1,2-dichloroethane, which has the following composition by weight:

dimethylsulfoxide: 50%
1,2-dichloroethane: 27.5% (trichloroethylene/1,2-dichloroethane molar ratio = 0.6160)
trichloroethylene: 22.5%

After partial vaporization, separation and condensation of the effluents, the trichloroethylene 1,1,2-dichloroethane molar ratio is 0.4779 in the liquid phase, and 0.7834 in the condensed vapor phase. The azeotrope is therefore strongly displaced, and the liquid phase is enriched with 1,2-dichloroethane, the relative "pseudo volatility" trichloroethylene/1,2-dichloroethane being 1.64.

EXAMPLE 3

Using the apparatus shown in FIG. 2, there is introduced into the boiler 11 a mixture of dimethylformamide, trichloroethylene and 1,2-dichloroethane, having the following composition by weight:

dimethylformamide: 50%
1,2-dichloroethane: 27.5% (trichloroethylene/1,2-dichlorethane molar ratio = 0.6160)
trichloroethylene: 22.5%

After partial vaporization, separation and condensation of the effluents, the trichloroethylene/1,2-dichloroethane molar ratio is 0.5290 in the liquid phase, and 0.7361 in the condensed vapor phase. The azeotrope is therefore displaced, and the liquid phase is enriched with 1,2-dichloroethane, the relative "pseudo volatility" trichloroethylene/1,2-dichloroethane being 1.39.

EXAMPLE 4

Into the boiler 11 of the apparatus shown in FIG. 2 is introduced a mixture of N-methyl pyrrolidone, trichloroethylene and 1,2-dichloroethane, having the following composition by weight:

N-methylpyrrolidone: 50%
1,2-dichloroethane: 27.5% (trichloroethylene/1,2-dichloroethane molar ratio = 0.6160)
trichloroethylene: 22.5%

After partial vaporization, separation and condensation of the effluents, the trichloroethylene/1,2-dichloroethane molar ratio is 0.5569 in the liquid phase, and 0.7076 in the condensed vapor phase.

The azeotrope is therefore displaced, and the liquid phase is enriched with 1,2-dichloroethane, the relative "pseudo volatility" trichloroethylene/1,2-dichloroethane being 1.27.

EXAMPLE 5

Using the apparatus shown in FIG. 2, into the boiler 11 is introduced a mixture of furfural, trichloroethylene and 1,2-dichloroethane, having the following composition by weight:

furfural: 50%
1,2-dichloroethane: 27.5% (trichloroethylene/1,2-dichloroethane molar ratio = 0.6160)
trichloroethylene: 22.5%

After partial vaporization, separation and condensation of the effluents, the trichloroethylene/1,2-dichloroethane molar ratio is 0.5209 in the liquid phase, and 0.7217 in the condensed vapor phase.

The azeotrope is therefore displaced, and the liquid phase is enriched with 1,2-dichloroethane, the relative "pseudo volatility" trichloroethylene/1,2-dichloroethane being 1.385.

EXAMPLE 6

In the apparatus shown in FIG. 2, there is introduced into the boiler 11 a mixture of diethylene glycol, trichloroethylene and 1,2-dichloroethane, having the following composition by weight:
 diethylene glycol: 50%
 1,2-dichloroethane: 27.5% (trichloroethylene/1,2-dichloroethane molar ratio = 0.6160)
 trichloroethylene: 22.5%

After partial vaporization, separation and condensation of the effluents, the trichloroethylene/1,2-dichloroethane molar ratio is 0.413 in the liquid phase, and 0.6954 in the condensed vapor phase.

The azeotrope is therefore displaced, and the liquid phase is enriched with 1,2-dichloroethane, the relative "pseudo volatility" trichloroethylene/1,2-dichloroethane being 1.684.

EXAMPLE 7

Introduced into the apparatus of previous Examples 2 to 6 is a mixture of triethylene glycol, trichloroethylene and 1,2-dichloroethylene, having the following composition by weight:
 triethylene glycol: 50%
 1,2-dichloroethane: 27.5% (trichloroethylene/1,2-dichloroethane molar ratio = 0.6160)
 trichloroethylene: 22.5%

After partial vaporization, separation and condensation of the effluents, the trichloroethylene/1,2-dichloroethane molar ratio is 0.4813 in the liquid phase, and 0.737 in the condensed vapor phase.

The azeotrope is therefore displaced, and the liquid phase is enriched with 1,2-dichloroethane, the relative "pseudo volatility" of trichloroethylene/1,2-dichloroethane being 1.53.

EXAMPLE 8

Into the apparatus of previous Examples 2 to 7, there is introduced a mixture of cyclohexanone, trichloroethylene and 1,2-dichloroethane, having the following composition by weight:
 cyclohexanone: 50%
 trichloroethylene: 22.5% (trichloroethylene/1,2-dichloroethane molar ratio = 0.6160)
 1,2-dichloroethane: 27.5%

After partial vaporization, separation and condensation of the effluents, the trichloroethylene/1,2-dichloroethane molar ratio is 0.6069 in the liquid phase and 0.6969 in the condensed vapor phase.

The azeotrope is therefore displaced, and the liquid phase is enriched with 1,2-dichloroethane, the relative "pseudo volatility" trichloroethylene/1,2-dichloroethane being 1.148.

EXAMPLE 9

Into the apparatus of previous Examples 2 to 8, there is introduced a mixture of propane diol, trichloroethylene and 1,2-dichloroethane, having the following composition by weight:
 propanediol: 50%
 trichloroethylene: 22.5% (trichloroethylene/1,2-dichloroethane molar ratio = 0.6160)
 1,2-dichloroethane: 27.5%

After partial vaporization, separation and condensation of the effluents, the trichloroethylene/1,2-dichloroethane molar ratio is 0.7015 in the condensed vapor phase, and 0.5285 in the liquid phase.

The azeotrope is therefore displaced, and the liquid phase is enriched with 1,2-dichloroethane, the relative "pseudo volatility" tricholoroethylene/1,2-dichloroethane being 1,327.

EXAMPLE 10

In the apparatus shown in FIG. 2, there is introduced into the boiler 11 a mixture of sulfolane, perchloroethylene and 1,1,2-trichloroethane, having the following composition by weight:
 sulfolane: 50%
 perchloroethylene: 28.5% (perchloroethylene/1,1,2-trichloroethane molar ratio - 1.066 (azeotrope mixture))
 1,2-trichloroethane: 21.5%

After partial vaporization, separation and condensation of the effluents, the perchloroethylene/1,1,2-trichloroethane molar ratio is 2.077 in the condensed vapor phase, and 0.584 in the liquid phase.

The azeotrope is therefore displaced, and the liquid phase is enriched with 1,1,2-trichloroethane, the relative "pseudo volatility" perchloroethylene/1,1,2-trichloroethane being 3.556.

By way of comparative testing, the following experiments were carried out, which illustrate the ineffectiveness of some organic compounds as regards a given separation operation.

TEST 1

In the apparatus shown in FIG. 2, there is introduced into the boiler 11, a mixture of hexycellosolve, trichloroethylene and 1,2-dichloroethane, having the following composition by weight:
 hexylcellosolve: 50%
 trichloroethylene: 22.5% (trichloroethylene/1,2-dichloroethane molar ratio = 0.6160)
 1,2-dichloroethane: 27.5%

After partial vaporization, separation and condensation of the effluents, the trichloroethylene/1,2-dichloroethane molar ratio is 0.6160 in the two collected phases. The relative "pseudo volatility" trichloroethylene/1,2-dichloroethane is 1.

TEST 2

Into the apparatus shown in FIG. 2, there is introduced a mixture of chlorinated paraffins made commercially available by the applicant under the name Alaiflex 50 A, trichloroethylene and 1,2-dichloroethane, having the following composition by weight:
 Alaiflex 50 A: 50%
 trichloroethylene: 22.5% (trichloroethylene/1,2-dichloroethane molar ratio = 0.6160)
 1,2-dichloroethane: 27.5%

After partial vaporization, separation and condensation of the effluents, the trichloroethylene/1,2-dichloroethane molar ratio is 0.6160 in the two collected phases. The relative "pseudo volatility" trichloroethylene/1,2-dichloroethane is 1.

I claim:

1. A method for at least partial separation of chlorinated aliphatic hydrocarbons having from 1—3 carbon atoms from mixtures consisting essentially of two or more of said chlorinated hyrocarbon by extractive distillation, comprising distilling the mixture of said chlorinated hydrocarbons with an organic compound having a boiling temperature which is higher than the $C_1$–$C_3$ chlorinated hydrocarbon to be separated, and selected from the group consisting of diethylene glycol, triethylene glycol, tetraethylene glycol, dipropylene glycol and propanediols, ethylene carbonate, propylene carbonate, dimethylformamide, furfural, N-methylpyrrolidone, cyclohexanone, dimethylsulfoxide, and sulfolane and alkylsulfolanes in which the alkyl group has from 1-2 carbon atoms, and in which the mixture of chlorinated aliphatic hydrocarbons comprises trichloroethylene and 1,2-dichloroethane.

2. A method for at least partial separation of chlorinated aliphatic hydrocarbons having from 1-3 carbon atoms from mixtures consisting essentially of two or more of said chlorinated hydrocarbons by extractive distillation; comprising distilling the mixture of said chlorinated hydrocarbons with an organic compound having a boiling temperature which is higher than the $C_1$-$C_3$ chlorinated hydrocarbon to be separated, and selected from the group consisting of diethylene glycol, triethylene glycol, tetraethylene glycol, dipropylene glycol and propanediols, ethylene carbonate, propylene carbonate, dimethylformamide, furfural, N-methylpyrrolidone, cyclohexanone, dimethylsulfoxide, and sulfolane and alkylsulfolanes in which the alkyl group has from 1-2 carbon atoms, and in which the mixture of chlorinated aliphatic hydrocarbons comprises perchloroethylene and 1,1,2-trichloroethane.

3. A method for at least partial separation of chlorinated aliphatic hydrocarbons having from 1-1 carbon atoms from mixtures consisting essentially of two or more of said chlorinated hydrocarbons by extractive distillation, comprising distilling the mixture of said chlorinated hydrocarbons with an organic compound having a boiling temperature which is higher than the $C_1$-$C_3$ chlorinated hydrocarbon to be separated, and selected from the group consisting of diethylene glycol, triethylene glycol, tetraethylene glycol, dipropylene glycol and propanediols, ethylene carbonate, propylene carbonate, dimethylformamide, furfural, N-methylpyrrolidone, cyclohexanone, dimethylsulfoxide, and sulfolane and alkylsulfolanes in which the alkyl group has from 1-2 carbon atoms, and in which the mixture of chlorinated aliphatic hydrocarbons comprises 1,2-dichloroethane and 1,1,1-trichloroethane.

4. A method for at least partial separation of chlorinated aliphatic hydrocarbons having from 1-1 carbon atoms from mixtures consisting essentially of two or more of said chlorinated hydrocarbons by extractive distillation, comprising distilling the mixture of said chlorinated hydrocarbons with an organic compound having a boiling temperature which is higher than the $C_1$-$C_3$ chlorinated hydrocarbon to be separated, and selected from the group consisting of diethylene glycol, triethylene glycol, tetraethylene glycol, dipropylene glycol and propanediols, ethylene carbonate, propylene carbonate, dimethylformamide, furfural, N-methylpyrrolidone, cyclohexanone, dimethylsulfoxide, and sulfolane and alkylsulfolanes in which the alkyl group has from 1-2 carbon atoms, and in which the mixture of chlorinated aliphatic hydrocarbons comprises carbon tetrachloride and 1,2-dichloroethane.

* * * * *

UNITED STATES PATENT OFFICE
CERTIFICATE OF CORRECTION

Patent No. 4,121,978  Dated October 24, 1978

Inventor(s) Jacques Becuwe

It is certified that error appears in the above-identified patent and that said Letters Patent are hereby corrected as shown below:

Col. 1, line 35, cancel "but" and substitute -- not --

Claims 3 and 4, line 2, change "1-1" to -- 1-3 --

Signed and Sealed this

First Day of May 1979

[SEAL]

Attest:

RUTH C. MASON  
Attesting Officer

DONALD W. BANNER  
Commissioner of Patents and Trademarks